(12) United States Patent
Tateyama et al.

(10) Patent No.: US 9,701,642 B2
(45) Date of Patent: Jul. 11, 2017

(54) METHOD FOR PRODUCING OPTICALLY ACTIVE 5-HYDROXY-3-KETOESTER

(71) Applicant: NISSAN CHEMICAL INDUSTRIES, LTD., Tokyo (JP)

(72) Inventors: Shouichi Tateyama, Funabashi (JP); Shinya Naitou, Funabashi (JP); Yasutaka Takada, Funabashi (JP); Mariko Ishida, Funabashi (JP); Hirohide Kitsuyama, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

(21) Appl. No.: 14/910,529

(22) PCT Filed: Aug. 26, 2014

(86) PCT No.: PCT/JP2014/072308
§ 371 (c)(1),
(2) Date: Feb. 5, 2016

(87) PCT Pub. No.: WO2015/030001
PCT Pub. Date: Mar. 5, 2015

(65) Prior Publication Data
US 2016/0185734 A1  Jun. 30, 2016

(30) Foreign Application Priority Data

Aug. 30, 2013  (JP) ................. 2013-179832

(51) Int. Cl.
| | | |
|---|---|---|
| *C07D 239/28* | (2006.01) | |
| *C07D 239/24* | (2006.01) | |
| *C07D 239/42* | (2006.01) | |
| *C07C 67/00* | (2006.01) | |
| *C07B 53/00* | (2006.01) | |
| *C07C 67/39* | (2006.01) | |
| *C07D 215/14* | (2006.01) | |

(52) U.S. Cl.
CPC ............ *C07D 239/42* (2013.01); *C07B 53/00* (2013.01); *C07C 67/00* (2013.01); *C07C 67/39* (2013.01); *C07D 215/14* (2013.01); *C07B 2200/07* (2013.01)

(58) Field of Classification Search
CPC ............................ C07D 239/28; C07D 239/24

USPC ................................................. 544/297, 335
See application file for complete search history.

(56) References Cited

FOREIGN PATENT DOCUMENTS

| | | |
|---|---|---|
| JP | 2009-500388 A | 1/2009 |
| WO | 03/042180 A1 | 5/2003 |
| WO | 2006/100689 A1 | 9/2006 |
| WO | 2006/106526 A1 | 10/2006 |
| WO | 2007/007119 A1 | 1/2007 |
| WO | 2007/017117 A1 | 2/2007 |
| WO | 2008/065410 A1 | 6/2008 |
| WO | 2008/096257 A1 | 8/2008 |
| WO | 2009/128091 A2 | 10/2009 |
| WO | 2011/121598 A1 | 10/2011 |

OTHER PUBLICATIONS

Dec. 21, 2016 Office Action issued in Chinese Patent Application No. 201480046836.3.
Soriente et. al., "Enantioselective Aldol Condensation of 1, 3-bis-(trimethylsilyloxy)-1-methoxy-buta-1,3-diene Promoted by Chiral Ti(IV)/Binol Complex" Tetrahedron: Asymmetry, vol. 11, pp. 2255-2258, (2000).
Soriente et. al., "An Efficient Asymmetric Aldol Reaction of Chan's Diene Promoted by Chiral Ti(IV)-Binol Complex", Tetrahedron: Asymmetry, vol. 12, pp. 959-963, (2001).
Xu et. al., "Achiral Additives Dramatically Enhance Enantioselectivities in the Binol-Ti(IV) Complex Catalyzed Aldol Condensations of Aldehydes With Chan's Diene", Tetrahedron: Asymmetry, vol. 21, pp. 156 to 158, (2010).
Nov. 4, 2014 Written Opinion issued in International Patent Application No. PCT/JP2014/012308.
Nov. 4, 2014 Search Report issued in International Patent Application No. PCT/JP2014/072308.

*Primary Examiner* — Charanjit Aulakh
(74) *Attorney, Agent, or Firm* — Oliff PLC

(57) ABSTRACT

The object of the present invention is to provide a method for producing in high yield with high stereoselectivity an optically active 5-hydroxy-3-ketoester compound which is useful as an intermediate for a pharmaceutical. A novel method for producing an optically active 5-hydroxy-3-ketoester compound in which an asymmetric aldol reaction by use of 1,3-diene compound is carried out in the presence of an optically active binaphthol-titanium complex together with a substituted nitrogen-containing 5 or 6-membered aromatic heterocyclic compound to obtain an optically active 5-hydroxy-3-ketoester compound in high yield with high stereoselectivity; and a novel production intermediate having a crystalline form.

11 Claims, 1 Drawing Sheet

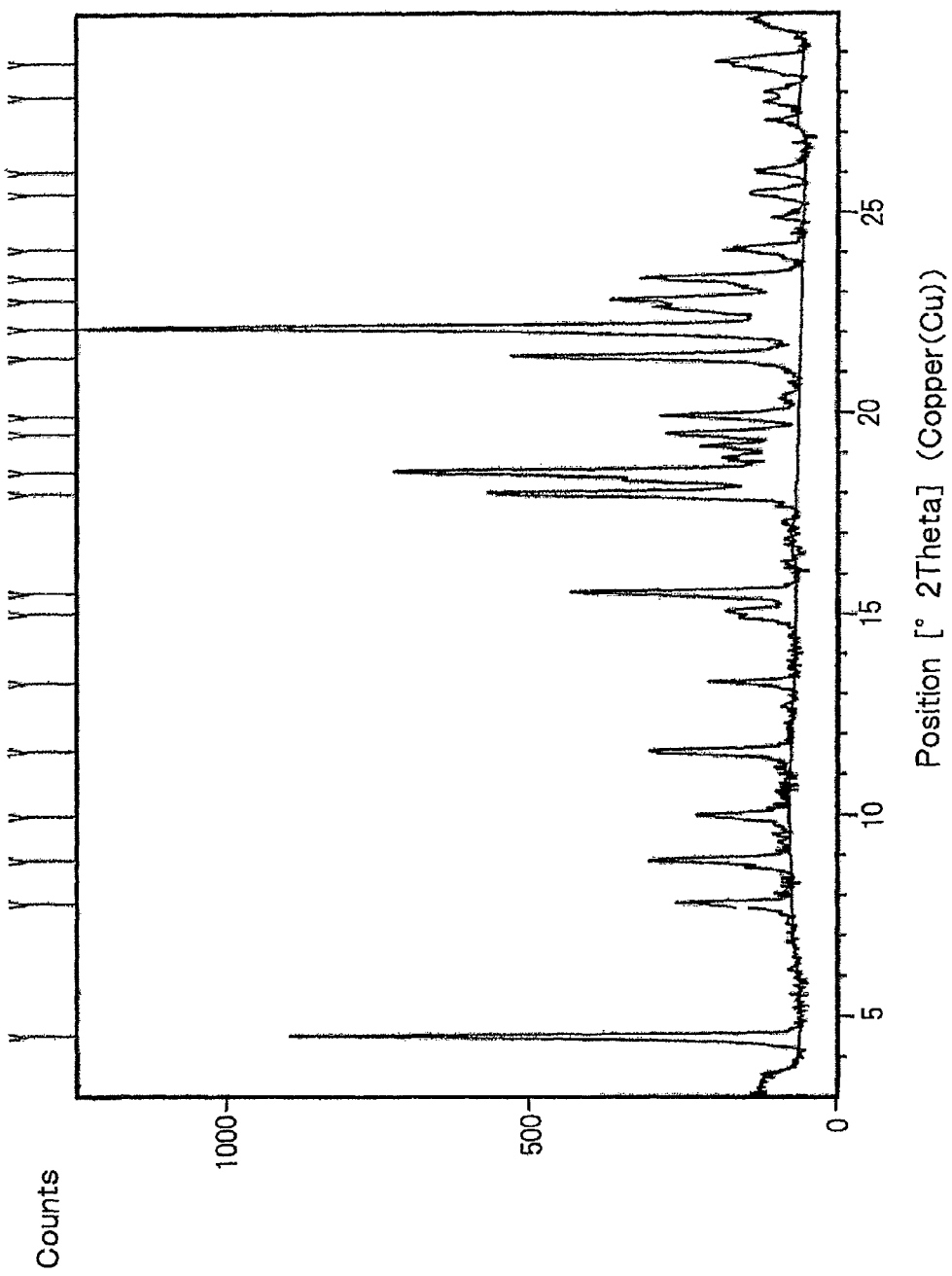

METHOD FOR PRODUCING OPTICALLY ACTIVE 5-HYDROXY-3-KETOESTER

TECHNICAL FIELD

The present invention relates to a method for producing an optically active 5-hydroxy-3-ketoester compound that is useful as a pharmaceutical intermediate using 1,3-bis-(trialkylsiloxy)-1-alkoxy-buta-1,3-diene. The present invention further relates to a novel pharmaceutical intermediate compound having a crystalline form that is obtained by the method described above.

BACKGROUND ART

As a method for synthesizing an optically active 5-hydroxy-3-ketoester compound, an asymmetric aldol reaction in which 1,3-bis-(trimethylsiloxy)-1-methoxy-buta-1,3-diene and an aldehyde are reacted in the presence of an optically active binaphthol-titanium complex under a low temperature condition has been reported (Non-Patent Document 1 and Non-Patent Document 2).

Subsequently, a reaction example in which high yield and high stereoselectivity are achieved by the same asymmetric aldol reaction in the presence of N,N,N',N'-tetramethylethylenediamine under a room temperature condition has been reported. However, in this report, a reactive substrate is limited to cinnamaldehyde. Furthermore, when an amine other than N,N,N',N'-tetramethylethylenediamine is used, the stereoselectivity decreases, and in particular, when a pyridine is used, the stereoselectivity largely decreases (Non-Patent Document 3).

Among the optically active 5-hydroxy-3-ketoester compounds described above, isopropyl (S,E)-7-[4-(4-fluorophenyl)-6-isopropyl-2-(N-methylmethylsulfonamido)pyrimidin-5-yl]-5-hydroxy-3-oxohept-6-enoate is a compound that has not been known. Therefore, a method for synthesizing the compound and a crystal of the compound are also unknown (for compounds of similar structure, see Patent Documents 1 to 6).

PRIOR ART DOCUMENTS

Patent Documents

Patent Document 1: International Publication WO 2006/106526
Patent Document 2: International Publication WO 2008/096257
Patent Document 3: International Publication WO 2008/065410
Patent Document 4: International Publication WO 2007/007119
Patent Document 5: International Publication WO 2007/017117
Patent Document 6: International Publication WO 2006/100689

Non-Patent Documents

Non-Patent Document 1: Tetrahedron: Asymmetry, 2000, vol. 11, pp. 2255 to 2258
Non-Patent Document 2: Tetrahedron: Asymmetry, 2001, vol. 12, pp. 959 to 963
Non-Patent Document 3: Tetrahedron: Asymmetry, 2010, vol. 21, pp. 156 to 158

SUMMARY OF THE INVENTION

Problem to be Solved by the Invention

It is an object of the present invention to provide a method for producing an optically active 5-hydroxy-3-ketoester compound in high yield with high stereoselectivity. It is another object of the present invention to provide a novel pharmaceutical intermediate compound obtained by the method described above.

Means for Solving the Problems

The inventors of the present invention have intensively studied the problems described above, and as a result, the inventors have found that the aforementioned asymmetric aldol reaction is carried out in the presence of an optically active binaphthol-titanium complex together with a substituted nitrogen-containing 5 or 6-membered aromatic heterocyclic compound to obtain an optically active 5-hydroxy-3-ketoester compound in high yield with high stereoselectivity.

In addition, the inventors have shown that isopropyl (S,E)-7-[4-(4-fluorophenyl)-6-isopropyl-2-(N-methylmethylsulfonamido)pyrimidin-5-yl]-5-hydroxy-3-oxohept-6-enoate can be synthesized as a novel compound by the production method. Among esters of (S,E)-7-[4-(4-fluorophenyl)-6-isopropyl-2-(N-methylmethylsulfonamido)pyrimidin-5-yl]-5-hydroxy-3-oxohept-6-enoic acid, a methyl ester, an ethyl ester, and a t-butyl ester thereof have been known. However, an isopropyl ester thereof has not been known. The esters are production intermediates of rosuvastatin calcium known as an HMG-CoA reductase inhibitor. Therefore, it is desirable that the esters be obtained with high purity. However, the properties of already existing esters are confirmed to be oils, and therefore there is a problem that the esters are unlikely to be purified industrially. The inventors have tried crystallization of the novel isopropyl ester as a pharmaceutical intermediate having properties that allow industrial purification. The inventors have intensively studied further, and as a result, succeeded the crystallization of the ester for the first time. Thus, the present invention has been accomplished.

Specifically, the present invention is characterized as follows:

(I) A method for producing an optically active 5-hydroxy-3-ketoester compound of Formula (4):

$$R^9 \!-\!\!(CH\!\!=\!\!CH)_n\!\!-\!\!\overset{OH}{\underset{}{\text{C}}}\!\!-\!\!\text{CH}_2\!\!-\!\!\overset{O}{\underset{}{\text{C}}}\!\!-\!\!\underset{R^8}{\text{CH}}\!\!-\!\!CO_2R^7 \quad (4)$$

(wherein $R^7$ is a $C_{1-6}$ alkyl group, a $C_{3-6}$ cycloalkyl group, a $C_{6-14}$ aryl group, or a $C_{7-16}$ aralkyl group, $R^8$ is a hydrogen atom, a $C_{1-6}$ alkyl group, a $C_{3-6}$ cycloalkyl group, a $C_{6-14}$ aryl group, or a $C_{7-16}$ aralkyl group, $R^9$ is an optionally substituted $C_{1-6}$ alkyl group, an optionally substituted $C_{3-6}$ cycloalkyl group, an optionally substituted $C_{6-14}$ aryl group, an optionally substituted $C_{7-16}$ aralkyl group, or an optionally substituted 5 to 10-membered heterocyclic group, and n is an integer of 0 or 1), characterized by comprising a step of reacting a 1,3-diene compound of Formula (2):

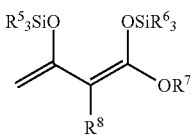

(wherein $R^5$ and $R^6$ are each independently a $C_{1-6}$ alkyl group, a $C_{3-6}$ cycloalkyl group, or a $C_{7-16}$ aralkyl group, and $R^7$ and $R^8$ are defined the same as in Formula (4)) with an aldehyde of Formula (3):

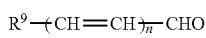

(wherein $R^9$ and n are defined the same as in Formula (4)) in the presence of an optically active binaphthol-titanium complex that is prepared from an optically active 1,1'-bi-2-naphthol compound of Formula (1):

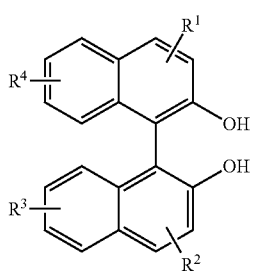

(wherein $R^1$, $R^2$, $R^3$, and $R^4$ are each independently a hydrogen atom, a halogen atom, a nitro group, a cyano group, a trialkylsilylethynyl group, an optionally substituted $C_{1-6}$ alkyl group, an optionally substituted $C_{3-6}$ cycloalkyl group, an optionally substituted $C_{1-4}$ alkoxy group, an optionally substituted $C_{3-4}$ cycloalkoxy group, an optionally substituted $C_{1-6}$ alkenyl group, an optionally substituted $C_{6-14}$ aryl group, an optionally substituted $C_{7-16}$ aralkyl group, or an optionally substituted 5 to 10-membered heterocyclic group) and a tetravalent titanium compound while a substituted nitrogen-containing 5 to 6-membered aromatic heterocyclic compound is allowed to coexist.

(II) The method according to (I), wherein
$R^1$, $R^2$, $R^3$, and $R^4$ are each a hydrogen atom,
$R^5$ and $R^6$ are methyl group,
$R^7$ is a $C_{1-6}$ alkyl group,
$R^8$ is a hydrogen atom,
$R^9$ is an optionally substituted $C_6$-14 aryl group or an optionally substituted 5 to 10-membered heterocyclic group, and
n is 1.

(III) The method according to (I) or (II), wherein $R^9$ is a $C_{6-14}$ aryl group, or a 5 to 10-membered heteroaryl group (the $C_{6-14}$ aryl group and the 5 to 10-membered heteroaryl group are not substituted or substituted by one substituent or two or more identical or different substituents selected from the substituent group A), the substituent group A includes a phenyl group, a phenyl group substituted by one or more halogen atoms, a $C_{1-6}$ alkyl group, a $C_{3-6}$ cycloalkyl group, and a $C_{1-6}$ alkyl ($C_{1-6}$ alkylsulfonyl)amino group.

(IV) The method according to (III), wherein $R^9$ is a 4-(4-fluorophenyl)-6-isopropyl-2-(N-methylmethylsulfonamido)pyrimidin-5-yl group, a 2-cyclopropyl-4-(4-fluorophenyl)quinolin-3-yl group, or phenyl group.

(V) The method according to any one of (I) to (IV), wherein the substituted nitrogen-containing 5 to 6-membered aromatic heterocyclic compound is pyrrole, imidazole, 1,2,3-triazole, or 1,2,4-triazole (the pyrrole, imidazole, 1,2,3-triazole, and 1,2,4-triazole are substituted by one or more substituents selected from the group consisting of a $C_{1-6}$ alkyl group, a $C_{3-6}$ cycloalkyl group, a $C_{1-4}$ alkoxy group, a $C_{3-4}$ cycloalkoxy group, and a di-$C_{1-6}$ alkylamino group).

(VI) The method according to (V), wherein the substituted nitrogen-containing 5 to 6-membered aromatic heterocyclic compound is 1-methylimidazole.

(VII) The method according to any one of (I) to (IV), wherein the substituted nitrogen-containing 5 to 6-membered aromatic heterocyclic compound is pyridine, pyridazine, pyrimidine, pyrazine, 1,2,3-triazine, 1,2,4-triazine, or 1,3,5-triazine (the pyridine, pyridazine, pyrimidine, pyrazine, 1,2,3-triazine, 1,2,4-triazine, and 1,3,5-triazine are substituted by one or more substituents selected from the group consisting of a $C_{1-6}$ alkyl group, a $C_{3-6}$ cycloalkyl group, a $C_{1-4}$ alkoxy group, a $C_{3-4}$ cycloalkoxy group, and a $C_{1-6}$ alkylamino group).

(VIII) The method according to (VII), wherein the substituted nitrogen-containing 5 to 6-membered aromatic heterocyclic compound is 4-methoxypyridine or N,N-dimethyl-4-aminopyridine.

(IX) Isopropyl (S,E)-7-[4-(4-fluorophenyl)-6-isopropyl-2-(N-methylmethylsulfonamido)pyrimidin-5-yl]-5-hydroxy-3-oxohept-6-enoate of Formula (5).

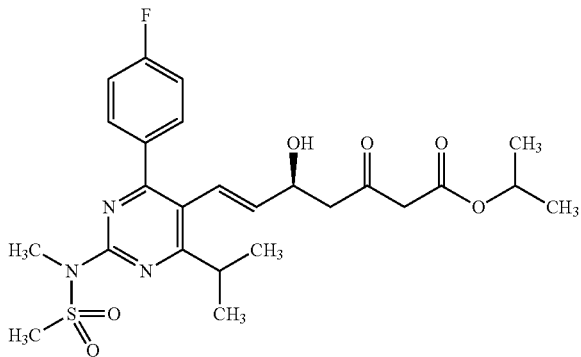

(X) A crystal of the isopropyl (S,E)-7-[4-(4-fluorophenyl)-6-isopropyl-2-(N-methylmethylsulfonamido)pyrimidin-5-yl]-5-hydroxy-3-oxohept-6-enoate according to (IX) having characteristic peaks at 2θ=4.5±0.2°, 8.9+0.2°, 11.6±0.2°, 15.5±0.2°, 18.0±0.2°, 18.5±0.2°, 19.5±0.2°, 19.9±0.2°, 21.4±0.2°, 22.1±0.2°, 22.8±0.2°, and 23.4±0.2° by powder X-ray diffraction measurement using Cu-Kα as a radiation source.

(XI) A crystal of the isopropyl (S,E)-7-[4-(4-fluorophenyl)-6-isopropyl-2-(N-methylmethylsulfonamido)pyrimidin-5-yl]-5-hydroxy-3-oxohept-6-enoate according to (IX) having characteristic peaks at 2θ=4.5°, 8.9°, 11.6°, 15.5°, 18.0°, 18.5°, 19.5°, 19.9°, 21.4°, 22.1°, 22.8°, and 23.4° by powder X-ray diffraction measurement using Cu-Kα as a radiation source.

Effects of the Invention

The present invention can provide a method for producing an optically active 5-hydroxy-3-ketoester compound in high yield with high stereoselectivity. The present invention can further provide a novel production intermediate compound having a crystalline form.

BRIEF DESCRIPTION OF THE DRAWINGS

FIG. 1 shows a powder X-ray diffraction pattern of crystal of isopropyl (S,E)-7-[4-(4-fluorophenyl)-6-isopropyl-2-(N-methylmethylsulfonamido)pyrimidin-5-yl]-5-hydroxy-3-oxohept-6-enoate of the present invention. In FIG. 1, a vertical axis represents a diffraction intensity (count), which means the number of counts of X-ray photons. A horizontal axis represents a diffraction angle 2θ)(°.

MODES FOR CARRYING OUT THE INVENTION

Hereinafter, the present invention will be further described in detail.

Terms Used Herein Will Be Described.

In the present specification, "n" means normal, "i" means iso, "s" means secondary, "t" means tertiary, and "c" means cyclo.

A $C_{1-6}$ alkyl group means an alkyl group having a carbon atom number of 1 to 6, that is, a linear or branched alkyl group having 1 to 6 carbon atoms. Specific examples thereof include methyl group, ethyl group, n-propyl group, i-propyl group, n-butyl group, i-butyl group, s-butyl group, t-butyl group, n-pentyl group, 2-methylbutyl group, 3-methylbutyl group, n-hexyl group, 2-methylpentyl group, 3-methylpentyl group, 4-methylpentyl group, 2-ethylbutyl group, and 3-ethylbutyl group.

A $C_{3-6}$ cycloalkyl group means a cycloalkyl group having a carbon atom number of 3 to 6, that is, a cyclic alkyl group having 3 to 6 carbon atoms. Specific examples thereof include c-propyl group, c-butyl group, c-pentyl group, and c-hexyl group.

A $C_{1-4}$ alkoxy group means an alkoxy group having a carbon atom number of 1 to 4, that is, a substituent in which a linear or branched alkyl group having 1 to 4 carbon atoms is bonded to an oxygen atom. Specific examples thereof include methoxy group, ethoxy group, n-propoxy group, i-propoxy group, n-butoxy group, i-butoxy group, s-butoxy group, and t-butoxy group.

A $C_{3-4}$ cycloalkoxy group means c-propoxy group or c-butoxy group.

A $C_{2-6}$ alkenyl group means an alkenyl group having a carbon atom number of 2 to 6, that is, a linear or branched alkenyl group having 2 to 6 carbon atoms and a double bond. Specific examples thereof include ethenyl group, 1-propenyl group, 2-propenyl group, 1-butenyl group, 2-butenyl group, and 3-butenyl group.

A $C_{6-14}$ aryl group means an aryl group having a carbon atom number of 6 to 14, that is, an aromatic hydrocarbon group having 6 to 14 carbon atoms. Specific examples thereof include phenyl group, 1-naphthyl group, 2-naphthyl group, 1-anthracenyl group, 2-anthracenyl group, 9-anthracenyl group, and biphenyl group.

A $C_{6-14}$ aryloxy group means a group in which one "$C_{6-14}$ aryl group" described above is bonded to an oxygen atom. Specific examples thereof include phenoxy group, 1-naphthyloxy group, and 2-naphthyloxy group.

A $C_{7-16}$ aralkyl group means an aralkyl group having a carbon atom number of 7 to 16, that is, an alkyl group that has an aromatic hydrocarbon as a substituent and has 7 to 16 carbon atoms in the whole substituent. Specific examples thereof include phenylmethyl group (benzyl group), 1-phenylethyl group, 2-phenylethyl group, 1-phenylpropyl group, 2-phenylpropyl group, 3-phenylpropyl group, naphthalen-1-ylmethyl group, naphthalen-2-ylmethyl group, naphthalen-1-ylethyl group, naphthalen-2-ylethyl group, anthracen-1-ylmethyl group, anthracen-2-ylmethyl group, and anthracen-9-ylmethyl group.

A 5 to 10-membered heterocyclic group means a monocyclic or fused-ring heterocyclic group in which the number of atoms constituting the ring is 5 to 10 and the atoms constituting the ring contain a heteroatom selected from the group consisting of a nitrogen atom, an oxygen atom, and a sulfur atom or two to four identical or different heteroatoms. The heterocyclic group may be saturated, partially unsaturated, or unsaturated. Specific examples thereof include pyrrolidinyl group, tetrahydrofuryl group, tetrahydrothienyl group, piperidyl group, tetrahydropyranyl group, tetrahydrothiopyranyl group, pyrrole group, furyl group, thienyl group, pyridyl group, pyrimidinyl group, pyridazinyl group, azepanyl group, oxepanyl group, thiepanyl group, azepinyl group, oxepinyl group, thiepinyl group, imidazolyl group, pyrazolyl group, oxazolyl group, thiazolyl group, imidazolynyl group, pyrazinyl group, morpholinyl group, thiadinyl group, indolyl group, isoindolyl group, benzimidazolyl group, purinyl group, quinolyl group, isoquinolyl group, quinoxalinyl group, cinnolinyl group, pteridinyl group, chromenyl group, and isochromenyl group.

A 5 to 10-membered heteroaryl group particularly means an unsaturated 5 to 10-membered heterocyclic group among the 5 to 10-membered heterocyclic groups described above.

A mono-$C_{1-6}$ alkylamino group means a group in which one hydrogen atom in an amino group is substituted by one "$C_{1-6}$ alkyl group" described above. Specific examples thereof include methylamino group, ethylamino group, n-propylamino group, i-propylamino group, n-butylamino group, i-butylamino group, t-butylamino group, n-pentylamino group, and n-hexylamino group.

A di-$C_{1-6}$ alkylamino group means a group in which two hydrogen atoms in an amino group are substituted by two identical or different "$C_{1-6}$ alkyl groups" described above. Specific examples thereof include dimethylamino group, diethylamino group, di-n-propylamino group, di-i-propylamino group, di-n-butylamino group, di-i-butylamino group, di-t-butylamino group, di-n-pentylamino group, di-n-hexylamino group, N-ethyl-N-methylamino group, N-methyl-N-n-propylamino group, N-isopropyl-N-methylamino group, N-n-butyl-N-methylamino group, N-i-butyl-N-methylamino group, N-t-butyl-N-methylamino group, N-methyl-N-n-pentylamino group, N-n-hexyl-N-methylamino group, N-ethyl-N-n-propylamino group, N-ethyl-N-i-propylamino group, N-n-butyl-N-ethylamino group, N-ethyl-N-i-butylamino group, N-t-butyl-N-ethylamino group, N-ethyl-N-n-pentylamino group, and N-ethyl-N-n-hexylamino group.

A $C_{1-4}$ alkoxycarbonyl group means a group in which one "$C_{1-4}$ alkoxy group" described above is bonded to a carbonyl group. Specific examples thereof include methoxycarbonyl group, ethoxycarbonyl group, n-propoxycarbonyl group, i-propoxycarbonyl group, n-butoxycarbonyl group, i-butoxycarbonyl group, and t-butoxycarbonyl group.

A $C_{1-6}$ alkylsulfonyl group means a group in which one "$C_{1-6}$ alkyl group" described above is bonded to a sulfonyl group. Specific examples thereof include methylsulfonyl group, ethylsulfonyl group, n-propylsulfonyl group, i-propylsulfonyl group, n-butylsulfonyl group, i-butylsulfonyl group, t-butylsulfonyl group, n-pentylsulfonyl group, and n-hexylsulfonyl group.

A $C_{1-6}$ alkylsulfonylamino group means a group in which one hydrogen atom in an amino group is substituted by one "$C_{1-6}$ alkylsulfonyl group" described above. Specific examples thereof include methylsulfonylamino group, ethylsulfonylamino group, n-propylsulfonylamino group, i-propylsulfonylamino group, n-butylsulfonylamino group, i-butylsulfonylamino group, t-butylsulfonylamino group, n-pentylsulfonylamino group, and n-hexylsulfonylamino group.

A bis($C_{1-6}$ alkylsulfonyl)amino group means a group in which two hydrogen atoms in an amino group are substituted by two identical or different "$C_{1-6}$ alkylsulfonyl groups" described above. Specific examples thereof include bis(methylsulfonyl)amino group, bis(ethylsulfonyl)amino group, bis(n-propylsulfonyl)amino group, bis(i-propylsulfonyl)amino group, bis(n-butylsulfonyl)amino group, bis(i-butylsulfonyl)amino group, bis(t-butylsulfonyl)amino group, bis(n-pentylsulfonyl)amino group, bis(n-hexylsulfonyl)amino group, N-ethylsulfonyl-N-methylsulfonylamino group, N-methylsulfonyl-N-n-propylsulfonylamino group, N-i-propylsulfonyl-N-methylsulfonylamino group, N-n-butylsulfonyl-N-methylsulfonylamino group, N-i-butylsulfonyl-N-methylsulfonylamino group, N-t-butylsulfonyl-N-methylsulfonylamino group, N-methylsulfonyl-N-n-pentylsulfonylamino group, N-n-hexylsulfonyl-N-methylsulfonylamino group, N-ethylsulfonyl-N-n-propylsulfonylamino group, N-ethylsulfonyl-N-i-propylsulfonylamino group, N-n-butylsulfonyl-N-ethylsulfonylamino group, N-ethylsulfonyl-N-i-butylsulfonylamino group, N-t-butylsulfonyl-N-ethylsulfonylamino group, N-ethylsulfonyl-N-n-pentylsulfonylamino group, and N-ethylsulfonyl-N-n-hexylsulfonylamino group.

A $C_{1-6}$ alkyl($C_{1-6}$ alkylsulfonyl)amino group, that is, an alkyl group having a carbon atom number of 1 to 6-(alkylsulfonyl having a carbon atom number of 1 to 6)amino group means a group in which two hydrogen atoms in an amino group are substituted by one "$C_{1-6}$ alkyl group" described above and one "$C_{1-6}$ alkylsulfonyl group" described above. Specific examples thereof include N-methyl-N-methylsulfonylamino group, N-ethyl-N-ethylsulfonylamino group, N-n-propyl-N-n-propylsulfonylamino group, N-i-propyl-N-i-propylsulfonylamino group, N-n-butyl-N-n-butylsulfonylamino group, N-i-butyl-N-i-butylsulfonylamino group, N-t-butyl-N-t-butylsulfonylamino group, N-n-pentyl-N-n-pentylsulfonylamino group, N-n-hexyl-N-n-hexylsulfonylamino group, N-ethyl-N-methylsulfonylamino group, N-methyl-N-n-propylsulfonylamino group, N-i-propyl-N-methylsulfonylamino group, N-n-propyl-N-methylsulfonylamino group, N-n-butyl-N-methylsulfonylamino group, N-t-butyl-N-methylsulfonylamino group, N-methyl-N-n-pentylsulfonylamino group, N-n-hexyl-N-methylsulfonylamino group, N-ethyl-N-n-propylsulfonylamino group, N-ethyl-N-i-propylsulfonylamino group, N-n-butyl-N-ethylsulfonylamino group, N-ethyl-N-i-butylsulfonylamino group, N-t-butyl-N-ethylsulfonylamino group, N-ethyl-N-n-pentylsulfonylamino group, and N-ethyl-N-n-hexylsulfonylamino group.

A halogen atom means a fluorine atom, a chlorine atom, a bromine atom, or an iodine atom.

"Optionally substituted" means unsubstituted or substituted by any number of optional substitutions.

"Substituted" means substituted by any number of optional substitutions.

The "optional substituents" described above are not particularly limited as long as the substituents do not adversely affect a reaction according to the present invention. Examples of the optional substituents include a $C_{1-6}$ alkyl group, a $C_{3-6}$ cycloalkyl group, a $C_{2-6}$ alkenyl group, a $C_{6-14}$ aryl group, a $C_{6-14}$ aryloxy group, a $C_{7-16}$ aralkyl group, a 5 to 10-membered heterocyclic group, a hydroxyl group, a $C_{1-4}$ alkoxy group, a $C_{3-4}$ cycloalkoxy group, an acetoxy group, a benzoyloxy group, an amino group, a mono-$C_{1-6}$ alkylamino group, a $C_{1-6}$ alkylsulfonylamino group, a N-acetylamino group, a di-$C_{1-6}$ alkylamino group, a bis($C_{1-6}$ alkylsulfonyl)amino group, a $C_{1-6}$ alkyl($C_{1-6}$ alkylsulfonyl)amino group, a N,N-diacetylamino group, a halogen atom, a $C_{1-4}$ alkoxycarbonyl group, a phenoxycarbonyl group, a N-methylcarbamoyl group, a N-phenylcarbamoyl group, a cyano group, a nitro group, and a carboxy group. Additional examples thereof include phenyl groups substituted by the aforementioned substituents.

A 5 to 6-membered nitrogen-containing aromatic heterocyclic compound means a monocyclic aromatic heteroaromatic compound in which the number of atoms constituting the ring is 5 to 6 and the atoms constituting the ring contain 1 to 4 nitrogen atoms. Specific examples thereof include pyrrole, pyrazole, imidazole, triazole, tetrazole, pyridine, pyridazine, pyrimidine, pyrazine, triazine, thiazole, isothiazole, oxazole, isoxazole, oxadiazole, and thiadiazole.

Next, preferable structures and preferable reaction conditions in the present invention will be described.

A 1,1'-bi-2-naphthol compound that is optically active binaphthol used in the method of the present invention is represented by Formula (1). In Formula (1), $R^1$, $R^2$, $R^3$, and $R^4$ are each independently a hydrogen atom, a halogen atom, a nitro group, a cyano group, a trialkylsilylethynyl group, an optionally substituted $C_{1-6}$ alkyl group, an optionally substituted $C_{3-6}$ cycloalkyl group, an optionally substituted $C_{1-4}$ alkoxy group, an optionally substituted $C_{3-4}$ cycloalkoxy group, an optionally substituted $C_{2-6}$ alkenyl group, an optionally substituted $C_{6-14}$ aryl group, or an optionally substituted 5 to 10-membered heterocyclic group, and are each preferably a hydrogen atom.

The tetravalent titanium compound in the present invention is not particularly limited as long as the reaction according to the present invention can be achieved.

A counterpart of titanium of the tetravalent titanium compound (hereinafter referred to as titanium substituent) may be an organic substance or an inorganic substance.

Specific examples of the titanium substituent include a halogen atom, an alkoxy group, or an oxygen atom. The halogen atom is preferably a chlorine atom, and the alkoxy group is preferably a $C_{1-4}$ alkoxy group or a $C_{3-4}$ cycloalkoxy group, and more preferably an isopropoxy group.

The tetravalent titanium compound is preferably halogenated titanium, dihalogenated dialkoxytitanium, or tetralkoxytitanium, more preferably titanium tetrachloride, dichloro-$C_{1-4}$ alkoxytitanium, dibromo-$C_{1-4}$ alkoxytitanium, or tetra-$C_{1-4}$ alkoxytitanium, further preferably tetra-$C_{1-4}$ alkoxytitanium, and particularly preferably tetraisopropoxytitanium.

The tetravalent titanium compound is preferably used in an amount of 0.5 molar equivalents to 2.0 molar equivalents, and more preferably 0.8 molar equivalents to 1.2 molar equivalents, relative to the optically active binaphthol.

An optically active binaphthol-titanium complex used in the method of the present invention is prepared, for example, in accordance with the method described in Patent Document 2. Specifically, the optically active binaphthol and titanium tetraisopropoxide are reacted in an organic solvent such as tetrahydrofuran and toluene. At that time, the optically active binaphthol-titanium complex is prepared by a method of allowing molecular sieves to coexist, or a method of adding water. The optically active binaphthol-titanium complex can be used in a concentrated and isolated form or in a solution form as it is in the next step. The optically active binaphthol-titanium complex is preferably used in an amount of 0.1% by mole to 50% by mole, and more preferably 0.5% by mole to 10% by mole, relative to an aldehyde.

A 1,3-diene compound used in the method of the present invention is represented by Formula (2). In Formula (2), $R^5$ and $R^6$ are each independently a $C_{1-6}$ alkyl group, a $C_{3-6}$ cycloalkyl group, or a $C_{7-16}$ aralkyl group, each preferably independently a $C_{1-6}$ alkyl group, and each more preferably a methyl group. $R^7$ is a $C_{1-6}$ alkyl group, a $C_{3-6}$ cycloalkyl group, a $C_{6-14}$ aryl group, or a $C_{7-16}$ aralkyl group, preferably a $C_{1-6}$ alkyl group, and more preferably a methyl group, an ethyl group, a n-propyl group, an i-propyl group, or a t-butyl group. $R^8$ is a hydrogen atom, a $C_{1-6}$ alkyl group, a $C_{3-6}$ cycloalkyl group, a $C_{6-14}$ aryl group, or a $C_{7-16}$ aralkyl group, and preferably a hydrogen atom.

This 1,3-diene compound is prepared, for example, in accordance with a method by Brownbridge et al. (Canadian Journal of Chemistry, 1983, vol. 61 (4), pp. 688 to 693). The 1,3-diene compound is used in an amount of 1.0 molar equivalent or more, preferably 1.0 molar equivalent to 3.0 molar equivalents, and more preferably 1.1 molar equivalents to 2.0 molar equivalents, relative to the aldehyde.

The aldehyde used in the method of the present invention is represented by Formula (3). In Formula (3), $R^9$ is preferably a $C_{6-14}$ aryl group or a 5 to 10-membered heteroaryl group (the $C_{6-14}$ aryl group and the 5 to 10-membered heteroaryl group are not substituted or are substituted by one substituent or two or more identical or different substituents selected from the substituent group A). The substituent group A includes phenyl group, phenyl group substituted by a halogen atom, a $C_{1-6}$ alkyl group, a $C_{3-6}$ cycloalkyl group, and a $C_{1-6}$ alkyl($C_{1-6}$ alkylsulfonyl)amino group, and is preferably a phenyl group, a pyrimidinyl group, or a quinolyl group (the phenyl group, the pyrimidinyl group, and the quinolyl group are not substituted or are substituted by one substituent or two or more identical or different substituents selected from the substituent group A). The substituent group A more preferably includes a phenyl group, a phenyl group substituted by one or more halogen atoms, a $C_{1-6}$ alkyl group, a $C_{3-6}$ cycloalkyl group, and a $C_{1-6}$ alkyl ($C_{1-6}$ alkylsulfonyl)amino group, and is more preferably a 4-(4-fluorophenyl)-6-isopropyl-2-(N-methylmethylsulfonamido)pyrimidin-5-yl group, a 2-cyclopropyl-4-(4-fluorophenyl)quinolin-3-yl group, or a phenyl group.

n is an integer of 0 or 1, and preferably 1.

A substituted nitrogen-containing 5 to 6-membered aromatic heterocyclic compound is preferably substituted pyrrole, substituted imidazole, substituted 1,2,3-triazole, or substituted 1,2,4-triazole. A preferable substituent in the compound is one or more substituents selected from the group consisting of a $C_{1-6}$ alkyl group, a $C_{3-6}$ cycloalkyl group, a $C_{1-4}$ alkoxy group, a $C_{3-4}$ cycloalkoxy group, and a $C_{1-6}$ alkylamino group. The compound is more preferably pyrrole substituted by a $C_{1-6}$ alkyl group, imidazole substituted by a $C_{1-6}$ alkyl group, 1,2,3-triazole substituted by a $C_{1-6}$ alkyl group, or 1,2,4-triazole substituted by a $C_{1-6}$ alkyl group, further preferably 1-methylpyrrole, 1-methylimidazole, 1-methyl-1H-1,2,3-triazole, 2-methyl-2H-1,2,3-triazole, 1-methyl-1H-1,2,4-triazole, or 4-methyl-4H-1,2,4-triazole, and particularly preferably 1-methylimidazole.

Further, the substituted nitrogen-containing 5 to 6-membered aromatic heterocyclic compound is preferably substituted pyridine, substituted pyridazine, substituted pyrimidine, substituted pyrazine, substituted 1,2,3-triazine, substituted 1,2,4-triazine, or substituted 1,3,5-triazine. A preferable substituent in the compound is one or more substituents selected from the group consisting of a $C_{1-6}$ alkyl group, a $C_{3-6}$ cycloalkyl group, a $C_{1-4}$ alkoxy group, a $C_{3-4}$ cycloalkoxy group, and a $C_{1-6}$ alkylamino group. The compound is more preferably pyridine substituted by a $C_{1-4}$ alkyl group, or pyridine substituted by a $C_{1-6}$ alkylamino group, and further preferably 4-methoxypyridine or N,N-dimethyl-4-aminopyridine.

The nitrogen-containing 5 to 6-membered aromatic heterocyclic compounds may be used singly or as a mixture of a plurality of these.

The reaction in the method of the present invention is preferably carried out in the presence of a solvent. The solvent used is not particularly limited as long as it does not inhibit the reaction. Preferred examples of the solvent include aliphatic hydrocarbons (hexane, heptane, etc.), aromatic hydrocarbons (benzene, toluene, xylene, etc.), ethers (diethyl ether, diisopropyl ether, tetrahydrofuran, 1,4-dioxane, t-butyl methyl ether, etc.), halogenated aliphatic hydrocarbons (methylene chloride, chloroform, dichloroethane, etc.), and nitriles (acetonitrile, propionitrile, etc.). Aromatic hydrocarbons and ethers are more preferred, toluene and tetrahydrofuran are further preferred, and tetrahydrofuran is particularly preferred.

The solvents may be used alone or as a mixture of a plurality of the solvents. In general, the amount of the solvent to be used depends on whether or not a substrate is crystalline, whether or not the viscosity is high, or the like. Therefore, the amount of the solvent to be used can be optionally determined according to the substrate, and is not limited as long as the substrate can be partially dissolved. In terms of effects of stirring efficiency and volume efficiency, the substrate concentration of aldehyde is generally 1% by weight to 80% by weight, preferably 3% by weight to 50% by weight, and more preferably 5% by weight to 20% by weight.

The reaction can be carried out at any temperature of −78° C. to the boiling point of a reaction medium. From the viewpoints of reaction operation and the industrial point of view, the temperature is generally −40° C. or higher and 60° C. or lower, preferably −20° C. or higher and 40° C. or lower, and more preferably −5° C. or higher and 40° C. or lower.

With respect to a reaction pattern, a mixture of the aldehyde, the 1,3-diene compound, the substituted nitrogen-containing 5 to 6-membered aromatic heterocyclic compound, and the solvent may be added to the optically active binaphthol-titanium complex that has been prepared in advance, or the aldehyde, the optically active binaphthol, the tetravalent titanium compound, the substituted nitrogen-containing 5 to 6-membered aromatic heterocyclic compound, and the 1,3-diene compound may be added in sequence. The addition order and method are not limited as long as they do not affect the reaction.

After completion of the reaction, an acid aqueous solution containing trifluoroacetic acid and sulfuric acid and the like is added to reaction solution and stirred to inactive a complex in the solution. A trialkylsilyl group is removed, and an alkaline solution such as an aqueous sodium carbonate solution is then added. The target compound is extracted by separation. The obtained organic phase is subjected to a purification operation such as column chromatography and crystallization. Thus, the target compound can be obtained.

Next, isopropyl (S,E)-7-[4-(4-fluorophenyl)-6-isopropyl-2-(N-methylmethylsulfonamido)pyrimidin-5-yl]-5-hydroxy-3-oxohept-6-enoate of Formula (5) that is the novel compound of the present invention will be described. The compound of Formula (5) can be produced by a reaction of (E)-N-[4-(4-fluorophenyl)-6-isopropyl-5-(3-oxoprop-1-en-1-yl)pyrimidin-2-yl]-N-metha nesulfoneamide with 1,3-bis-(trimethylsiloxy)-1-isopropoxybuta-1,3-diene in the method of the present invention.

As described above, as esters of (S,E)-7-[4-(4-fluorophenyl)-6-isopropyl-2-(N-methylmethylsulfonamido)pyrimidin-5-yl]-5-hydroxy-3-oxohept-6-enoic acid, a methyl ester, an ethyl ester, and a t-butyl ester thereof have been known. Hereinafter, the respective esters will be described as references.
(1) Methyl ester
CAS No. 912337-61-2 (5S,6E), 890028-67-8 (6E)
Property: yellow oil
Source: International Publication WO 2006/106526
(2) Ethyl ester
CAS No. 901765-36-4 (5S,6E)
Property: oil
Source: International Publication WO 2008/096257, International Publication WO 2008/065410, and International Publication WO 2007/007119 (Patent Document 2, Patent Document 3, and Patent Document 4)
(3) t-butyl ester
CAS No. 910867-13-9 (5S,6E), 947262-23-9 (6E)
Property: oil (Patent Document 2), brown oil (Patent Document 5), or orange oil (Patent Document 6)
Source: International Publication WO 2008/096257, International Publication WO 2007/017117, and International Publication WO 2006/100689

For a crystallization operation of the compound of Formula (5), an alcohol solvent, an ester solvent, or an aromatic hydrocarbon solvent is used.

The alcohol solvent to be used is an alcohol having 1 to 4 carbon atoms such as methanol, ethanol, n-propanol, i-propanol, n-butanol, s-butanol, t-butanol and the like and preferably i-propanol.

The ester solvent to be used is a formate ester (methyl formate, ethyl formate, and n-propyl formate), or acetate ester (methyl acetate, ethyl acetate, n-propyl acetate, i-propyl acetate, n-butyl acetate, i-butyl acetate, and t-butyl acetate), and preferably ethyl acetate.

The aromatic hydrocarbon solvent to be used is an aromatic hydrocarbon having 6 to 8 carbon atoms (benzene, toluene, and xylene), and preferably toluene.

These solvents may be used as a mixture with other solvents at any mixing ratio.

These solvents may be used for crystallization in an amount of 1 part by weight to 100 parts by weight, preferably 2 parts by weight to 20 parts by weight, and more preferably 5 parts by weight to 15 parts by weight, relative to 1 g of the target compound of Formula (5).

The crystallization is carried out by any one of a method of cooling after heating and dissolving, a method of concentrating after dissolving, and a method of adding low-soluble solvent (poor solvent) after dissolving, or a combination of these.

The crystallization temperature falls within a range of −20° C. to 60° C., and preferably −10° C. to 50° C. unless otherwise stated.

For the crystallization, a seed crystal can be used. The seed crystal can be obtained by a method known by those skilled in the art, the method in which a wall of a container containing a solution of the target compound is rubbed with a spatula.

Characteristics of a crystal, particularly a difference from another crystalline form (crystal polymorphism) can be analyzed by powder X-ray diffraction measurement. A position of peak (peak value) obtained by the powder X-ray diffraction measurement is represented by 2θ. The unit of 2θ is degree (°). The peak value may vary depending on measurement conditions. In a case where a crystalline form of a sample is identified by comparing the measured peak of the sample with the peak value of a standard substance, when the crystalline forms are identical, the peak value of the sample and the peak value of the standard substance are generally equal within a difference of 0.2° (see The Japanese Pharmacopoeia 16th edition). Therefore, a peak value according to the compound of the present invention allows a difference within about ±0.2°, and is identified. Accordingly, when the peak value according to the compound of the present invention is compared with the measured peak value of the target sample, a peak having a difference within about ±0.2° is regarded as identical diffraction peak. Thus, the identification can be carried out. However, the peak value may be affected by measurement devices and measurement conditions. Therefore, a difference of crystalline form can be finally confirmed by comprehensive analysis of the measurement condition, the peak value, the diffraction pattern, and the like.

EXAMPLES

Hereinafter, the present invention will be described specifically with reference to Examples, but the scope of the present invention is not limited to these Examples.

A structure of a product was confirmed by $^1$H-NMR in ECP-300 manufactured by JEOL Ltd. Hereinafter, $^1$H-NMR data described is represented by a chemical shift δ (unit: ppm) (division pattern, integrated value) of signal using tetramethylsilane as an internal standard substance. In a described division pattern, "s" means singlet, "d" means doublet, "t" means triplet, "septet" means septet, "dd" means double doublet, "m" means multiplet, "J" means coupling constant, and "CDCl$_3$" means deuterated chloroform.

Powder X-ray diffraction was measured by X'PertPRO (radiation source: Cu-Kα, wavelength: 1.54060 ($10^{-10}$ m)) manufactured by PANalytical B.V. Differential scanning calorimetry was measured by DSC1 manufactured by Mettler-Toledo International Inc.

Reference Example 1

Preparation of (S)-(−)-binaphthol-titanium Complex Solution 4.41 g of toluene was added to 0.7570 g (2.65 mmol) of (S)-(−)-1,1'-bi-2-naphthol and mixed at 0° C. to 10° C. To the mixed liquid, a mixed solution of 0.7571 g (2.65 mmol) of titanium tetraisopropoxide, 0.0477 g (2.65 mmol) of water, and 2.28 g of tetrahydrofuran was added dropwise, and 1.12 g of tetrahydrofuran was further added. The resultant mixture was stirred for 20 minutes to obtain an (S)-(−)-binaphthol-titanium complex solution.

Example 1

Synthesis of Isopropyl (S,E)-7-[4-(4-fluorophenyl)-6-isopropyl-2-(N-methylmethylsulfonamido)pyrimidin-5-yl]-5-hydroxy-3-oxohept-6-enoate Using N,N-dimethyl-4-aminopyridine 10.00 g (26.49 mmol) of (E)-N-[4-(4-fluorophenyl)-6-isopropyl-5-(3-oxoprop-1-en-1-yl)pyrimidin-2-yl]-N-methyl methanesulfoneamide and 48.03 g of tetrahydrofuran were mixed and stirred at room temperature for 10 minutes. To this solution, 1.83 g (0.53 mmol) of the (S)-(−)-binaphthol-titanium complex solution prepared in accordance with the method of Reference Example 1 was added, and the mixture was washed with 2.01 g of tetrahydrofuran. In addition, 1.30 g (10.60 mmol) of N,N-dimethyl-4-aminopyridine and 17.61 g (45.04 mmol) of 1,3-bis-(trimethylsiloxy)-1-isopropoxybuta-1,3-diene were added, and the resultant solution was stirred at room temperature for 22 hours. Subsequently, 30.01 g of tetrahydrofuran was added to this solution, 7.83 g (39.74 mmol) of aqueous solution of 50% sulfuric acid was then added dropwise, and the resultant solution was stirred at room temperature for 1 hour. To the solution, 25.30 g (23.85 mmol) of aqueous solution of 10% sodium carbonate was further added, and the resultant solution was stirred at room temperature for 30 minutes, and separated to obtain an organic phase. The obtained organic phase was washed with 29.53 g of 20% salt solution, and separated to obtain 100.00 g of organic phase. The organic phase was concentrated under reduced pressure to obtain 30.30 g of solution. To the solution, 100.13 g of ethyl acetate was added, and the resultant solution was concentrated again under reduced pressure to obtain 26.07 g of solution. Then 19.99 g of n-heptane was added. An insoluble substance was collected by filtration through Celite®, and washed with a mixed solution of 2.00 g of ethyl acetate and 2.01 g of n-heptane. To the combined solution of the filtrate and the washing liquid, 20.05 g of ethyl acetate and 20.08 g of n-heptane were added, the resultant solution was heated to 50° C., stirred for 5 minutes, cooled to 25° C., and stirred for 120 minutes. To this solution, 40.00 g of n-heptane was further added dropwise over 60 minutes, and the resultant mixture was stirred in an ice bath for 16 hours. A solid deposited during stirring in the ice bath was collected by filtration, washed with a mixed solution of 3.80 g of ethyl acetate and 8.27 g of n-heptane, and dried at 50° C. under reduced pressure to obtain 11.52 g (22.09 mmol) of isopropyl (S,E)-7-[4-(4-fluorophenyl)-6-isopropyl-2-(N-methylmethylsulfonamido)pyrimidin-5-yl]-5-hydroxy-3-oxohept-6-enoate as a pale yellow solid. The isolated yield was 83.4%, and the optical purity was 99.46% ee.

$^1$H-NMR (CDCl$_3$)

δ ppm: 1.25-1.27 (m, 12H), 2.64-2.66 (m, 2H), 2.91 (d, 1H, J=4.1 Hz), 3.32-3.38 (m, 1H), 3.41 (s, 2H), 3.51 (s, 3H), 3.57 (s, 3H), 4.61-4.68 (m, 1H), 5.06 (septet, 1H, J=6.1 Hz), 5.44 (dd, 1H, J=5.1, 16.2 Hz), 6.67 (dd, 1H, J=1.7, 16.0 Hz), 7.15-7.60 (m, 2H), 7.60-7.67 (m, 2H)

The optical purity was calculated as an enantiomeric excess (% ee) by high performance liquid chromatography analysis using a column for separation of optical isomer.

Column: CHIRALPAK IA (manufactured by DAICEL CORPORATION)
Eluent: n-hexane/methanol/diethylamine=970/30/3 V/V/V
Eluent flow rate: 1.0 mL/min
Detection wavelength: 245 nm The powder X-ray diffraction of crystal obtained in Example 1 was measured, and the following characteristic peaks and particularly characteristics peaks are confirmed.

(Characteristic Peaks)
2θ=4.5°, 8.9°, 11.6°, 15.5°, 18.0°, 18.5°, 19.5°, 19.9°, 21.4°, 22.1°, 22.8°, 23.4°

(Particularly Characteristic Peaks)
2θ=4.5°, 15.5°, 18.0°, 18.5°, 21.4°, 22.1°, 22.8°

A powder X-ray diffraction pattern obtained in the measurement is shown in FIG. 1.

In Examples 2 and 3, a reaction yield was calculated by quantitative analysis using high performance liquid chromatography with the compound obtained in Example 1 used as a standard substance and diethyl phthalate used as an internal standard substance.

Column: L-column ODS (manufactured by Chemicals Evaluation and Research Institute, Japan)
Eluent: aqueous solution of methanol-0.01 M ammonium acetate, 65:35
Eluent flow rate: 0.4 mL/min
Detection wavelength: 250 nm

Example 2

Synthesis of Isopropyl (S,E)-7-[4-(4-fluorophenyl)-6-isopropyl-2-(N-methylmethylsulfonamido)pyrimidin-5-yl]-5-hydroxy-3-oxohept-6-enoate Using 4-methoxypyridine The title compound was obtained by the same operation as in Example 1 except that the used amount of (E)-N-[4-(4-fluorophenyl)-6-isopropyl-5-(3-oxoprop-1-en-1-yl)pyrimidin-2-yl]-N-methanesulfoneamide was changed to 5.00 g (13.2 mmol) and 0.58 g (5.30 mmol) of 4-methoxypyridine was used instead of N,N-dimethyl-4-aminopyridine. As other reagents, the same reagents as those in Example 1 were used (provided that the molar equivalents of the other used reagents were the same as the amounts relative to the amount of aldehyde in Example 1). The quantitative yield was 92.1%, and the optical purity was 99.75% ee.

Example 3

Synthesis of Isopropyl (S,E)-7-[4-(4-fluorophenyl)-6-isopropyl-2-(N-methylmethylsulfonamido)pyrimidin-5-yl]-5-hydroxy-3-oxohept-6-enoate Using N-methylimidazole The title compound was obtained by the same operation as in Example 1 except that the used amount of (E)-N-[4-(4-fluorophenyl)-6-isopropyl-5-(3-oxoprop-1-en-1-yl)pyrimidin-2-yl]-N-methyl methanesulfoneamide was changed to 5.00 g (13.2 mmol) and 0.44 g (5.30 mmol) of N-methylimidazole was used instead of N,N-dimethyl-4-aminopyridine. As other reagents, the same reagents as those in Example 1 were used (provided that the molar equivalents of the other used reagents were the same as the amounts relative to the amount of aldehyde in Example 1). The quantitative yield was 88.2%, and the optical purity was 99.13% ee.

In Examples 4 and 5, a reaction yield was calculated by quantitative analysis using high performance liquid chromatography with isopropyl (S,E)-7-[2-cyclopropyl-4-(4-fluorophenyl)quinolin-3-yl]-5-hydroxy-3-oxohept-6-enoate obtained by a method described in International Publication WO 2003/042180 used as a standard substance and diethyl phthalate used as an internal standard substance.

Column: L-column ODS (manufactured by Chemicals Evaluation and Research Institute, Japan)
Eluent: aqueous solution of methanol-0.01 M ammonium acetate, 75:25, V/V
Eluent flow rate: 0.4 mL/min
Detection wavelength: 250 nm The optical purity was calculated as an enantiomeric excess (% ee) by high performance liquid chromatography analysis using a column for separation of optical isomer.
Column: CHIRALPAK AD-H (manufactured by DAICEL CORPORATION)
Eluent: n-hexane/ethanol/diethylamine=950/50/5, V/V/V
Eluent flow rate: 0.5 mL/min
Detection wavelength: 245 nm Example 4

Synthesis of Isopropyl (S,E)-7-[2-cyclopropyl-4-(4-fluorophenyl)quinolin-3-yl]-5-hydroxy-3-oxohept-6-enoate Using N,N-dimethyl-4-aminopyridine 5.00 g (15.75 mmol) of (E)-3-[2-cyclopropyl-4-(4-fluorophenyl)quinolin-3-yl]acrylaldehyde and 24.00 g of tetrahydrofuran were mixed and stirred at room temperature for 10 minutes. To this solution, 1.09 g (0.32 mmol) of the (S)-(−)-binaphthol-titanium complex solution prepared in accordance with the method of Reference Example 1 was then added, and the resultant mixture was washed with 1.00 g of tetrahydrofuran. 0.77 g (6.30 mmol) of N,N-dimethyl-4-aminopyridine and 10.47 g (26.78 mmol) of 1,3-bis-(trimethylsiloxy)-1-isopropoxybuta-1,3-diene were added, and the resultant mixture was stirred at room temperature for 22 hours. Subsequently, 15.02 g of tetrahydrofuran was added, 4.64 g (23.63 mmol) of aqueous solution of 50% sulfuric acid was then added dropwise, and the resultant mixture was stirred at room temperature for 1 hour. To the resultant mixture, 15.03 g (14.18 mmol) of aqueous solution of 10% sodium carbonate was further added, and the resultant mixture was stirred at room temperature for 30 minutes, and separated to obtain an organic phase. The quantitative yield was 97.5%, and the optical purity was 99.29% ee.

Example 5

Synthesis of Isopropyl (S,E)-7-[2-cyclopropyl-4-(4-fluorophenyl)quinolin-3-yl]-5-hydroxy-3-oxohept-6-enoate Using N-methylimidazole The title compound was obtained by the same operation as in Example 4 except that 0.51 g (6.30 mmol) of N-methylimidazole was used instead of N,N-dimethyl-4-aminopyridine used in Example 4. As other reagents, the same reagents as those in Example 4 were used. The quantitative yield was 96.2%, and the optical purity was 99.28% ee.

Example 6

Synthesis of Isopropyl (S,E)-5-hydroxy-3-oxo-7-phenylhept-6-enoate Using N,N-dimethyl-4-aminopyridine To a mixed solution of 3.00 g (22.70 mmol) of cinnamaldehyde and 14.40 g of tetrahydrofuran, 1.61 g (equivalent to 0.45 mmol) of the (S)-(−)-binaphthol-titanium complex solution prepared in accordance with the method of Reference Example 1 was added, and the resultant mixture was washed with 0.60 g of tetrahydrofuran. 1.10 g (9.08 mmol) of N,N-dimethyl-4-aminopyridine and 10.23 g (equivalent to 38.59 mmol) of 1,3-bis-(trimethylsiloxy)-1-isopropoxybuta-1,3-diene were added, and the resultant mixture was stirred at room temperature for 22 hours. Subsequently, 9.00 g of tetrahydrofuran was added, 6.68 g (34.05 mmol) of aqueous solution of 50% sulfuric acid was then added dropwise, and the resultant mixture was stirred at room temperature for 1 hour. To the resultant mixture, 21.65 g (20.43 mmol) of aqueous solution of 10% sodium carbonate was further added, and the resultant mixture was stirred at room temperature for 30 minutes, and separated to obtain 39.55 g of organic phase. The resultant organic phase was concentrated under reduced pressure, and then purified by silica gel column chromatography (hexane/ethyl acetate=70/30) to obtain isopropyl (S,E)-5-hydroxy-3-oxo-7-phenylhept-6-enoate. The isolated yield was 96.9%, and the optical purity was 95.43% ee.
$^1$H-NMR (CDCl$_3$)
δ ppm:1.26 (d, 6H, J=6.1 Hz), 2.77-2.95 (m, 2H), 3.48 (s, 2H), 4.72-4.85 (m, 1H), 4.98-5.14 (m, 1H), 6.20 (dd, 1H, J=6.1, 15.7 Hz), 6.65 (dd, 1H, J=1.0, 15.7 Hz), 7.18-7.42 (m, 5H)

The optical purity was calculated as an enantiomeric excess (% ee) by high performance liquid chromatography analysis using a column for separation of optical isomer.
Column: CHIRALPAK AD (manufactured by DAICEL CORPORATION)
Eluent: n-hexane/ethanol/diethylamine=950/50, V/V, containing 0.01% of trifluoroacetic acid
Eluent flow rate: 1.0 mL/min
Detection wavelength: 254 nm Example 7

Synthesis of Isopropyl (S,E)-5-hydroxy-3-oxo-7-phenylhept-6-enoate Using N-methylimidazole The title compound was obtained by the same operation as in Example 6 except that 0.75 g (9.08 mmol) of N-methylimidazole was used instead of N,N-dimethyl-4-aminopyridine used in Example 6. As other reagents, the same reagents as those in Example 6 were used. The isolated yield was 95.5%, and the optical purity was 93.85% ee.

INDUSTRIAL APPLICABILITY

The present invention is useful in that an optically active 5-hydroxy-3-ketoester compound useful as a pharmaceutical intermediate can be produced in high yield with high stereoselectivity. The present invention is further useful in that a novel production intermediate compound having a crystalline form can be provided.

The invention claimed is:
1. A method for producing an optically active 5-hydroxy-3-ketoester compound of Formula (4):

$$R^9 \!\!-\!\!(CH\!\!=\!\!CH\!\!-\!\!)_n \overset{OH}{\underset{}{\text{C}}}\overset{}{\underset{R^8}{\text{C}}}\!\!-\!\!CO_2R^7 \qquad (4)$$

(wherein, $R^7$ is a $C_{1-6}$ alkyl group, a $C_{3-6}$ cycloalkyl group, a $C_{6-14}$ aryl group, or a $C_{7-16}$ aralkyl group, $R^8$ is a hydrogen atom, a $C_{1-6}$ alkyl group, a $C_{3-6}$ cycloalkyl group, a $C_{6-14}$ aryl group, or a $C_{7-16}$ aralkyl group, $R^9$ is an optionally substituted pyrimidine group, and n is an integer of 0 or 1), comprising a step of reacting a 1,3-diene compound of Formula (2):

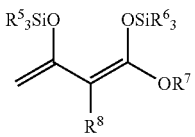
(2)

(wherein $R^5$ and $R^6$ are each independently a $C_{1-6}$ alkyl group, a $C_{3-6}$ cycloalkyl group, or a $C_{7-16}$ aralkyl group, and $R^7$ and $R^8$ are defined the same as in Formula (4)) with an aldehyde of Formula (3):

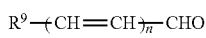
(3)

(wherein $R^9$ and n are defined the same as in Formula (4)) in the presence of an optically active binaphthol-titanium complex that is prepared from an optically active 1,1'-bi-2-naphthol compound of Formula (1):

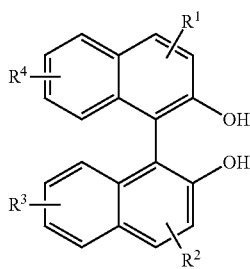
(1)

(wherein $R^1$, $R^2$, $R^3$, and $R^4$ are each independently a hydrogen atom, a halogen atom, a nitro group, a cyano group, a trialkylsilylethynyl group, an optionally substituted $C_{1-6}$ alkyl group, an optionally substituted $C_{3-6}$ cycloalkyl group, an optionally substituted $C_{1-4}$ alkoxy group, an optionally substituted $C_{3-4}$ cycloalkoxy group, an optionally substituted $C_{1-6}$ alkenyl group, an optionally substituted $C_{6-14}$ aryl group, an optionally substituted $C_{7-16}$ aralkyl group, or an optionally substituted 5 to 10-membered heterocyclic group) and a tetravalent titanium compound while a substituted nitrogen-containing 5 to 6-membered aromatic heterocyclic compound is allowed to coexist.

2. The method according to claim 1, wherein
$R^1$, $R^2$, $R^3$, and $R^4$ are each a hydrogen atom,
$R^5$ and $R^6$ are methyl group,
$R^7$ is a $C_{1-6}$ alkyl group,
$R^8$ is a hydrogen atom,
$R^9$ is an optionally substituted pyrimidine group, and
n is 1.

3. The method according to claim 1, wherein $R^9$ is a pyrimidine group that is not substituted or substituted by one substituent or two or more identical or different substituents selected from the substituent group A, the substituent group A includes a phenyl group, a phenyl group substituted by one or more halogen atoms, a $C_{1-6}$ alkyl group, a $C_{3-6}$ cycloalkyl group, and a $C_{1-6}$ alkyl($C_{1-6}$ alkylsulfonyl)amino group.

4. The method according to claim 3, wherein $R^9$ is a 4-(4-fluorophenyl)-6-isopropyl-2-(N-methylmethylsulfonamido)pyrimidin-5-yl group.

5. The method according to claim 1, wherein the substituted nitrogen-containing 5 to 6-membered aromatic heterocyclic compound is pyrrole, imidazole, 1,2,3-triazole, or 1,2,4-triazole (the pyrrole, imidazole, 1,2,3-triazole, and 1,2,4-triazole are substituted by one or more substituents selected from the group consisting of a $C_{1-6}$ alkyl group, a $C_{3-6}$ cycloalkyl group, a $C_{1-4}$ alkoxy group, a $C_{3-4}$ cycloalkoxy group, and a di-$C_{1-6}$alkylamino group).

6. The method according to claim 5, wherein the substituted nitrogen-containing 5 to 6-membered aromatic heterocyclic compound is 1-methylimidazole.

7. The method according to claim 1, wherein the substituted nitrogen-containing 5 to 6-membered aromatic heterocyclic compound is pyridine, pyridazine, pyrimidine, pyrazine, 1,2,3-triazine, 1,2,4-triazine, or 1,3,5-triazine (the pyridine, pyridazine, pyrimidine, pyrazine, 1,2,3-triazine, 1,2,4-triazine, and 1,3,5-triazine are substituted by one or more substituents selected from the group consisting of a $C_{1-6}$ alkyl group, a $C_{3-6}$ cycloalkyl group, a $C_{1-4}$ alkoxy group, a $C_{3-4}$ cycloalkoxy group, and a di-$C_{1-6}$ alkylamino group).

8. The method according to claim 7, wherein the substituted nitrogen-containing 5 to 6-membered aromatic heterocyclic compound is 4-methoxypyridine or N,N-dimethyl-4-aminopyridine.

9. Isopropyl (S,E)-7-[4-(4-fluorophenyl)-6-isopropyl-2-(N-methylmethylsulfonamido)pyrimidin-5-yl]-5-hydroxy-3-oxohept-6-enoate of Formula (5)

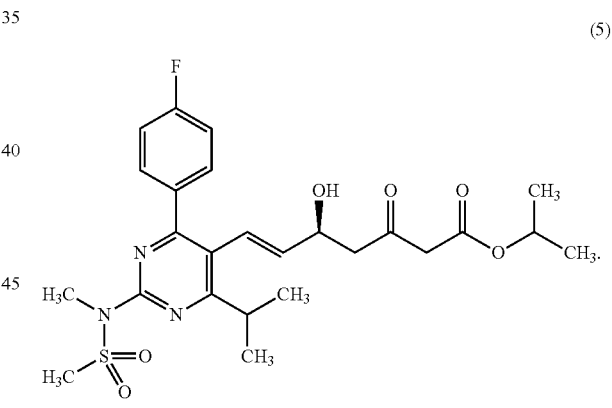
(5)

10. A crystal of the isopropyl (S,E)-7-[4-(4-fluorophenyl)-6-isopropyl-2-(N-methylmethylsulfonamido)pyrimidin-5-yl]-5-hydroxy-3-oxohept-6-enoate according to claim 9 having characteristic peaks at 2θ=4.5±0.2°, 8.9±0.2°, 11.6±0.2°, 15.5±0.2°, 18.0±0.2°, 18.5±0.2°, 19.5±0.2°, 19.9±0.2°, 21.4±0.2°, 22.1±0.2°, 22.8±0.2°, and 23.4±0.2° by powder X-ray diffraction measurement using Cu-Kα as a radiation source.

11. A crystal of the isopropyl (S,E)-7-[4-(4-fluorophenyl)-6-isopropyl-2-(N-methylmethylsulfonamido)pyrimidin-5-yl]-5-hydroxy-3-oxohept-6-enoate according to the claim 9 having characteristic peaks at 2θ=4.5°, 8.9°, 11.6°, 15.5°, 18.0°, 18.5°, 19.5°, 19.9°, 21.4°, 22.1°, 22.8°, and 23.4° by powder X-ray diffraction measurement using Cu-Kα as a radiation source.

* * * * *